US010092663B2

(12) United States Patent
Constant et al.

(10) Patent No.: US 10,092,663 B2
(45) Date of Patent: Oct. 9, 2018

(54) POLYMERS

(71) Applicant: MicroVention, Inc., Tustin, CA (US)

(72) Inventors: Michael Constant, Mission Viejo, CA (US); Gregory M. Cruise, Rancho Santa Margarita, CA (US); Samuel Chen, Tustin, CA (US)

(73) Assignee: Terumo Corporation, Tokyo (JP)

( * ) Notice: Subject to any disclaimer, the term of this patent is extended or adjusted under 35 U.S.C. 154(b) by 122 days.

(21) Appl. No.: 14/678,468

(22) Filed: Apr. 3, 2015

(65) Prior Publication Data

US 2015/0306255 A1 Oct. 29, 2015

Related U.S. Application Data

(60) Provisional application No. 61/986,018, filed on Apr. 29, 2014.

(51) Int. Cl.
A61K 9/00 (2006.01)
A61K 49/04 (2006.01)
D01F 6/28 (2006.01)
D01D 5/00 (2006.01)
D01D 5/38 (2006.01)
D01F 1/10 (2006.01)
A61L 31/14 (2006.01)
A61L 31/16 (2006.01)
A61L 31/18 (2006.01)

(52) U.S. Cl.
CPC ...... A61K 49/0404 (2013.01); A61K 49/0409 (2013.01); A61L 31/145 (2013.01); A61L 31/148 (2013.01); A61L 31/16 (2013.01); A61L 31/18 (2013.01); D01D 5/00 (2013.01); D01D 5/38 (2013.01); D01F 1/10 (2013.01); D01F 6/28 (2013.01); A61L 2430/36 (2013.01); D10B 2509/00 (2013.01)

(58) Field of Classification Search
None
See application file for complete search history.

(56) References Cited

U.S. PATENT DOCUMENTS

| 3,709,842 | A | 1/1973 | Stoy et al. |
| 3,749,085 | A | 7/1973 | Wilson et al. |
| 4,020,829 | A | 5/1977 | Wilson et al. |
| 4,301,803 | A | 11/1981 | Handa et al. |
| 4,304,232 | A | 12/1981 | Michaels |
| 4,365,621 | A | 12/1982 | Brundin |
| 4,402,319 | A | 9/1983 | Handa et al. |
| 4,493,329 | A | 1/1985 | Crawford et al. |
| 4,509,504 | A | 4/1985 | Brundin |
| 4,529,739 | A | 7/1985 | Scott et al. |
| 4,551,132 | A | 11/1985 | Pasztor et al. |
| 4,663,358 | A | 5/1987 | Hyon et al. |
| 4,795,741 | A | 1/1989 | Leshchiner et al. |
| 4,819,637 | A | 4/1989 | Dormandy, Jr. et al. |
| 4,932,419 | A | 6/1990 | de Toledo |
| 4,951,677 | A | 8/1990 | Crowley et al. |
| 4,994,069 | A | 2/1991 | Ritchart et al. |
| 5,120,349 | A | 6/1992 | Stewart et al. |
| 5,122,136 | A | 6/1992 | Guglielmi et al. |
| 5,129,180 | A | 7/1992 | Stewart |
| 5,133,731 | A | 7/1992 | Butler et al. |
| 5,147,646 | A | 9/1992 | Graham |
| 5,154,705 | A | 10/1992 | Fleischhacker et al. |
| 5,163,952 | A | 11/1992 | Froix |
| 5,165,421 | A | 11/1992 | Fleischhacker et al. |
| 5,217,484 | A | 6/1993 | Marks |
| 5,226,911 | A | 7/1993 | Chee et al. |
| 5,258,042 | A | 11/1993 | Mehta |
| 5,304,194 | A | 4/1994 | Chee et al. |
| 5,312,415 | A | 5/1994 | Palermo |
| 5,350,397 | A | 9/1994 | Palermo et al. |
| 5,354,290 | A | 10/1994 | Gross |
| 5,373,619 | A | 12/1994 | Fleischhacker et al. |
| 5,382,259 | A | 1/1995 | Phelps et al. |
| 5,382,260 | A | 1/1995 | Dormandy, Jr. et al. |
| 5,443,478 | A | 8/1995 | Purdy |
| 5,449,369 | A | 9/1995 | Imran |
| 5,456,693 | A | 10/1995 | Conston et al. |
| 5,469,867 | A | 11/1995 | Schmitt |
| 5,476,472 | A | 12/1995 | Dormandy, Jr. et al. |
| 5,483,022 | A | 1/1996 | Mar |
| 5,522,822 | A | 6/1996 | Phelps et al. |
| 5,525,334 | A | 6/1996 | Ito et al. |
| 5,536,274 | A | 7/1996 | Neuss |

(Continued)

FOREIGN PATENT DOCUMENTS

| CA | 2551373 C | 6/2014 |
| CN | 102107025 B | 5/2014 |

(Continued)

OTHER PUBLICATIONS

Ahuja et al., Platinum coil coatings to increase thrombogenicity: a preliminary study in rabbits, AJNR, 14: 794-789 (1993).
Almany, Biomaterials, 26, 2005, 2467-2477, Biosynthetic hydrogel scaffolds made from fibrinogen and polyethylene glycol for 3D cell cultures.
Carelli V. et al., "Silicone microspheres for pH-controlled gastrointestinal drug delivery," 1999, International Journal of Pharmaceutics, V179, p. 73-83.
Chirila et al., Poly(2-hydroxyethyl metharcrylate) sponges ans implant materials: in vivo and in vitro evaluation of cellular invasion. Biomaterials, 14(1):26-38 (1993).
Constant et al., Preparation, Characterization, and Evaluation of Radiopaque Hydrogel Filaments for Endovascular Embolization. Journal of Biomedical Materials Research Part B: Applied Biomaterials, vol. 89B, No. 2, pp. 306-313 (2008).

(Continued)

Primary Examiner — James W Rogers
(74) Attorney, Agent, or Firm — K&L Gates LLP; Louis C. Cullman; Brian J. Novak

(57) ABSTRACT

Polymers are described herein comprising: a reaction product of a prepolymer solution including at least one macromer, at least one flexomer, and at least one visualization agent. Methods of making and using these polymers are also described.

11 Claims, 2 Drawing Sheets

(56) References Cited

U.S. PATENT DOCUMENTS

| | | |
|---|---|---|
| 5,541,234 A | 7/1996 | Unger et al. |
| 5,549,624 A | 8/1996 | Mirigian |
| 5,573,520 A | 11/1996 | Schwartz et al. |
| 5,573,994 A | 11/1996 | Kabra et al. |
| 5,578,074 A | 11/1996 | Mirigian |
| 5,580,568 A | 12/1996 | Greff et al. |
| 5,582,610 A | 12/1996 | Grossi et al. |
| 5,582,619 A | 12/1996 | Ken |
| 5,607,417 A | 3/1997 | Batich et al. |
| 5,609,629 A | 3/1997 | Fearnot et al. |
| 5,612,050 A | 3/1997 | Rowe et al. |
| 5,624,461 A | 4/1997 | Mariant |
| 5,624,685 A | 4/1997 | Takahashi et al. |
| 5,634,936 A | 6/1997 | Linden et al. |
| 5,645,558 A | 7/1997 | Horton |
| 5,651,979 A | 7/1997 | Ron et al. |
| 5,658,308 A | 8/1997 | Snyder |
| 5,667,767 A | 9/1997 | Greff et al. |
| 5,672,634 A | 9/1997 | Tseng et al. |
| 5,678,296 A | 10/1997 | Fleischhacker et al. |
| 5,690,666 A | 11/1997 | Berenstein et al. |
| 5,690,667 A | 11/1997 | Gia |
| 5,690,671 A | 11/1997 | McGurk et al. |
| 5,695,480 A | 12/1997 | Evans et al. |
| 5,702,361 A | 12/1997 | Evans et al. |
| 5,718,711 A | 2/1998 | Berenstein et al. |
| 5,725,568 A | 3/1998 | Hastings |
| 5,749,894 A | 5/1998 | Engelson |
| 5,750,585 A | 5/1998 | Park et al. |
| 5,752,974 A | 5/1998 | Rhee et al. |
| 5,755,658 A | 5/1998 | Wallace et al. |
| 5,766,160 A | 6/1998 | Samson et al. |
| 5,766,219 A | 6/1998 | Horton |
| 5,823,198 A | 10/1998 | Jones et al. |
| 5,830,178 A | 11/1998 | Jones et al. |
| 5,843,743 A | 12/1998 | Hubbell et al. |
| 5,851,508 A | 12/1998 | Greff et al. |
| 5,853,419 A | 12/1998 | Ken et al. |
| 5,883,705 A | 3/1999 | Minne et al. |
| 5,891,155 A | 4/1999 | Irie |
| 5,952,232 A | 9/1999 | Rothman |
| 5,976,162 A | 11/1999 | Doan et al. |
| 5,980,514 A | 11/1999 | Kupiecki et al. |
| 6,004,338 A | 12/1999 | Ken et al. |
| 6,004,573 A | 12/1999 | Rathi et al. |
| 6,013,084 A | 1/2000 | Ken et al. |
| 6,015,424 A | 1/2000 | Rosenbluth et al. |
| 6,017,977 A | 1/2000 | Evans et al. |
| 6,051,607 A | 4/2000 | Greff |
| 6,063,100 A | 5/2000 | Diaz et al. |
| 6,066,149 A | 5/2000 | Samson et al. |
| 6,093,199 A | 7/2000 | Brown et al. |
| 6,096,034 A | 8/2000 | Kupiecki et al. |
| 6,103,865 A | 8/2000 | Bae et al. |
| 6,136,015 A | 10/2000 | Kurz et al. |
| 6,146,373 A | 11/2000 | Cragg et al. |
| 6,159,165 A | 12/2000 | Ferrera et al. |
| 6,168,570 B1 | 1/2001 | Ferrera |
| 6,171,326 B1 | 1/2001 | Ferrera et al. |
| 6,179,857 B1 | 1/2001 | Diaz et al. |
| 6,187,024 B1 | 2/2001 | Boock et al. |
| 6,193,728 B1 | 2/2001 | Ken et al. |
| 6,201,065 B1 | 3/2001 | Pathak et al. |
| 6,231,590 B1 | 5/2001 | Slaikeu et al. |
| 6,238,403 B1 | 5/2001 | Greene, Jr. et al. |
| 6,245,090 B1 | 6/2001 | Gilson et al. |
| 6,270,748 B1 | 8/2001 | Annan et al. |
| 6,280,457 B1 | 8/2001 | Wallace et al. |
| 6,281,263 B1 | 8/2001 | Evans et al. |
| 6,287,318 B1 | 9/2001 | Villar et al. |
| 6,299,604 B1 | 10/2001 | Ragheb et al. |
| 6,299,619 B1 | 10/2001 | Greene, Jr. et al. |
| 6,299,627 B1 | 10/2001 | Eder et al. |
| 6,303,100 B1 | 10/2001 | Ricci et al. |
| 6,312,421 B1 | 11/2001 | Boock |
| 6,333,020 B1 | 12/2001 | Wallace et al. |
| 6,335,384 B1 | 1/2002 | Evans et al. |
| 6,342,202 B1 | 1/2002 | Evans et al. |
| 6,399,886 B1 | 6/2002 | Avellanet |
| 6,423,085 B1 | 7/2002 | Murayama et al. |
| 6,425,893 B1 | 7/2002 | Guglielmi et al. |
| 6,454,738 B1 | 9/2002 | Tran et al. |
| 6,503,244 B2 | 1/2003 | Hayman |
| 6,511,468 B1 | 1/2003 | Cragg et al. |
| 6,511,472 B1 | 1/2003 | Hayman et al. |
| 6,531,111 B1 | 3/2003 | Whalen et al. |
| 6,537,569 B2 | 3/2003 | Cruise et al. |
| 6,558,367 B1 | 5/2003 | Cragg et al. |
| 6,565,551 B1 | 5/2003 | Jones et al. |
| 6,569,190 B2 | 5/2003 | Whalen et al. |
| 6,599,448 B1 | 7/2003 | Ehrhard, Jr. et al. |
| 6,602,261 B2 | 8/2003 | Greene, Jr. et al. |
| 6,605,294 B2 | 8/2003 | Sawhney |
| 6,623,450 B1 | 9/2003 | Dutta |
| 6,634,361 B1 | 10/2003 | Nikolchev et al. |
| 6,645,167 B1 | 11/2003 | Whalen et al. |
| 6,684,884 B2 | 2/2004 | Nikolchev et al. |
| 6,699,222 B1 | 3/2004 | Jones et al. |
| 6,723,108 B1 | 4/2004 | Jones et al. |
| 6,756,031 B2 | 6/2004 | Evans et al. |
| 6,759,028 B2 | 7/2004 | Wallace et al. |
| 6,849,081 B2 | 2/2005 | Sepetka et al. |
| 6,860,893 B2 | 3/2005 | Wallace et al. |
| 6,878,384 B2 | 4/2005 | Cruise et al. |
| 6,887,974 B2 | 5/2005 | Pathak et al. |
| 6,962,689 B2 | 11/2005 | Whalen et al. |
| 6,964,657 B2 | 11/2005 | Cragg et al. |
| 7,018,365 B2 | 3/2006 | Strauss et al. |
| 7,033,374 B2 | 4/2006 | Schaefer et al. |
| 7,066,904 B2 | 6/2006 | Rosenthal et al. |
| 7,070,607 B2 | 7/2006 | Murayama et al. |
| 7,083,643 B2 | 8/2006 | Whalen et al. |
| 7,138,106 B2 | 11/2006 | Evans et al. |
| 7,374,568 B2 | 5/2008 | Whalen et al. |
| 7,422,569 B2 | 9/2008 | Wilson et al. |
| 7,459,142 B2 | 12/2008 | Greff |
| 7,476,648 B1 | 1/2009 | Tabata et al. |
| 7,507,229 B2 | 3/2009 | Hewitt et al. |
| 7,507,394 B2 | 3/2009 | Whalen et al. |
| 7,976,527 B2 | 7/2011 | Cragg et al. |
| 7,988,992 B2 | 8/2011 | Omidian et al. |
| 8,066,667 B2 | 11/2011 | Hayman et al. |
| 8,235,941 B2 | 8/2012 | Hayman et al. |
| 8,377,091 B2 | 2/2013 | Cruise et al. |
| 8,454,649 B2 | 6/2013 | Cragg et al. |
| 8,486,046 B2 | 7/2013 | Hayman et al. |
| 9,011,884 B2 | 4/2015 | Constant et al. |
| 2001/0023325 A1 | 9/2001 | Ferrera |
| 2002/0026234 A1 | 2/2002 | Li et al. |
| 2002/0042378 A1 | 4/2002 | Reich et al. |
| 2002/0169473 A1 | 11/2002 | Sepetka et al. |
| 2002/0176880 A1 | 11/2002 | Cruise et al. |
| 2003/0021762 A1 | 1/2003 | Luthra et al. |
| 2003/0077272 A1 | 4/2003 | Pathak et al. |
| 2003/0078339 A1 | 4/2003 | Kiser et al. |
| 2003/0086874 A1 | 5/2003 | Whalen, II et al. |
| 2003/0100942 A1 | 5/2003 | Ken et al. |
| 2003/0134032 A1 | 7/2003 | Chaouk |
| 2003/0203991 A1* | 10/2003 | Schottman ............... C08K 3/22 523/334 |
| 2003/0211083 A1 | 11/2003 | Vogel et al. |
| 2003/0220245 A1 | 11/2003 | Hubbell et al. |
| 2003/0232198 A1 | 12/2003 | Lamberti et al. |
| 2003/0232895 A1 | 12/2003 | Omidian et al. |
| 2004/0006534 A1 | 1/2004 | Schaefer et al. |
| 2004/0024098 A1 | 2/2004 | Mather et al. |
| 2004/0059370 A1 | 3/2004 | Greene et al. |
| 2004/0091543 A1 | 5/2004 | Bell et al. |
| 2004/0098028 A1 | 5/2004 | Martinez |
| 2004/0115164 A1 | 6/2004 | Pierce et al. |
| 2004/0158282 A1 | 8/2004 | Jones et al. |
| 2004/0209998 A1 | 10/2004 | De Vries |
| 2005/0003010 A1 | 1/2005 | Cohen et al. |
| 2005/0008610 A1 | 1/2005 | Schwarz et al. |

(56) References Cited

U.S. PATENT DOCUMENTS

| | | |
|---|---|---|
| 2005/0095428 A1 | 5/2005 | DiCarlo et al. |
| 2005/0106119 A1 | 5/2005 | Brandom et al. |
| 2005/0119687 A1 | 6/2005 | Dacey et al. |
| 2005/0143484 A1 | 6/2005 | Fang et al. |
| 2005/0171572 A1 | 8/2005 | Martinez et al. |
| 2005/0175709 A1 | 8/2005 | Baty et al. |
| 2005/0196426 A1 | 9/2005 | Cruise et al. |
| 2005/0196449 A1 | 9/2005 | DiCarlo et al. |
| 2005/0226935 A1 | 10/2005 | Kamath et al. |
| 2005/0281883 A1 | 12/2005 | Daniloff et al. |
| 2006/0052815 A1 | 3/2006 | Fitz et al. |
| 2006/0067883 A1 | 3/2006 | Krom et al. |
| 2006/0074370 A1 | 4/2006 | Zhou |
| 2006/0233854 A1 | 10/2006 | Seliktar et al. |
| 2007/0026039 A1 | 2/2007 | Drumheller et al. |
| 2007/0196454 A1 | 8/2007 | Stockman et al. |
| 2007/0202046 A1 | 8/2007 | Dave |
| 2007/0208141 A1 | 9/2007 | Shull et al. |
| 2007/0224234 A1 | 9/2007 | Steckel et al. |
| 2007/0231366 A1 | 10/2007 | Sawhney et al. |
| 2007/0237720 A1 | 10/2007 | Padilla et al. |
| 2007/0237741 A1 | 10/2007 | Figuly et al. |
| 2007/0248567 A1 | 10/2007 | Pathak et al. |
| 2007/0254005 A1 | 11/2007 | Pathak et al. |
| 2007/0288084 A1 | 12/2007 | Lee et al. |
| 2008/0019921 A1 | 1/2008 | Zhang |
| 2008/0038354 A1 | 2/2008 | Slager et al. |
| 2008/0039890 A1 | 2/2008 | Matson et al. |
| 2008/0114277 A1 | 5/2008 | Ambrosio et al. |
| 2008/0208167 A1 | 8/2008 | Stankus |
| 2008/0226741 A1 | 9/2008 | Richard |
| 2008/0281352 A1 | 11/2008 | Ingenito et al. |
| 2009/0041850 A1 | 2/2009 | Figuly |
| 2009/0048659 A1 | 2/2009 | Weber et al. |
| 2009/0054535 A1 | 2/2009 | Figuly et al. |
| 2009/0081275 A1 | 3/2009 | Rolfes et al. |
| 2009/0093550 A1 | 4/2009 | Rolfes et al. |
| 2009/0117033 A1 | 5/2009 | O'Gara |
| 2009/0164013 A1 | 6/2009 | Cruise et al. |
| 2009/0181068 A1 | 7/2009 | Dunn |
| 2009/0221731 A1 | 9/2009 | Vetrecin et al. |
| 2009/0232869 A1 | 9/2009 | Greene |
| 2009/0259302 A1 | 10/2009 | Trollsas et al. |
| 2010/0010159 A1 | 1/2010 | Belcheva |
| 2010/0023112 A1 | 1/2010 | Borck et al. |
| 2010/0036491 A1 | 2/2010 | He et al. |
| 2010/0042067 A1 | 2/2010 | Koehler |
| 2010/0086678 A1 | 4/2010 | Arthur et al. |
| 2010/0092533 A1 | 4/2010 | Stopek et al. |
| 2010/0241160 A1 | 9/2010 | Murphy |
| 2010/0247663 A1 | 9/2010 | Day et al. |
| 2010/0249913 A1 | 9/2010 | Dattaa et al. |
| 2010/0256777 A1 | 10/2010 | Dattta et al. |
| 2010/0303804 A1 | 12/2010 | Liska et al. |
| 2011/0008406 A1 | 1/2011 | Altman et al. |
| 2011/0008442 A1 | 1/2011 | Zawko et al. |
| 2011/0020236 A1 | 1/2011 | Bohmer et al. |
| 2011/0091549 A1 | 4/2011 | Blaskovich et al. |
| 2011/0182998 A1 | 7/2011 | Reb et al. |
| 2011/0184455 A1 | 7/2011 | Keeley |
| 2011/0190813 A1 | 8/2011 | Brownlee et al. |
| 2011/0202016 A1 | 8/2011 | Zugates et al. |
| 2011/0212178 A1 | 9/2011 | Constant et al. |
| 2012/0041481 A1 | 2/2012 | Daniloff et al. |
| 2012/0083523 A1 | 4/2012 | Richard et al. |
| 2012/0114589 A1 | 5/2012 | Rolfes-Meyering et al. |
| 2012/0156164 A1 | 6/2012 | Park et al. |
| 2012/0164100 A1 | 6/2012 | Li et al. |
| 2012/0184642 A1 | 7/2012 | Bartling et al. |
| 2012/0238644 A1 | 9/2012 | Gong et al. |
| 2012/0244198 A1 | 9/2012 | Malmsjo et al. |
| 2012/0283769 A1 | 11/2012 | Cruise et al. |
| 2012/0289995 A1 | 11/2012 | Constant et al. |
| 2013/0039848 A1 | 2/2013 | Bradbury et al. |
| 2013/0045182 A1 | 2/2013 | Gong et al. |
| 2013/0060230 A1 | 3/2013 | Capistron et al. |
| 2013/0079421 A1 | 3/2013 | Aviv et al. |
| 2013/0108574 A1 | 5/2013 | Chevalier et al. |
| 2013/0131716 A1 | 5/2013 | Cruise et al. |
| 2013/0253087 A1 | 9/2013 | Cruise et al. |
| 2014/0056806 A1 | 2/2014 | Vernengo et al. |
| 2014/0274945 A1 | 9/2014 | Blaskovich et al. |
| 2014/0277057 A1 | 9/2014 | Ortega et al. |
| 2015/0190553 A1 | 7/2015 | Constant et al. |
| 2015/0283306 A1 | 10/2015 | Constant et al. |
| 2015/0306227 A1 | 10/2015 | Cruise et al. |

FOREIGN PATENT DOCUMENTS

| | | |
|---|---|---|
| EP | 809519 B1 | 12/1997 |
| EP | 1599258 B1 | 8/2008 |
| EP | 1601392 B1 | 4/2009 |
| WO | 1991/016057 A | 10/1991 |
| WO | 1994/003155 A1 | 2/1994 |
| WO | 1997/022365 A1 | 6/1997 |
| WO | 1997/026939 A1 | 7/1997 |
| WO | 1997/027888 A1 | 8/1997 |
| WO | 1998/001421 A1 | 1/1998 |
| WO | 1998/043615 A1 | 10/1998 |
| WO | 1999/023954 A1 | 5/1999 |
| WO | 1999/044538 A1 | 9/1999 |
| WO | 1999/056783 A1 | 11/1999 |
| WO | 1999/065401 A1 | 12/1999 |
| WO | 2000/027445 A1 | 5/2000 |
| WO | 2000/038651 A1 | 7/2000 |
| WO | 2000/074577 A1 | 12/2000 |
| WO | 2001/068720 A1 | 9/2001 |
| WO | 2002/005731 A1 | 1/2002 |
| WO | 2002/096302 A1 | 12/2002 |
| WO | 2003/043552 A1 | 5/2003 |
| WO | 2005/032337 A2 | 4/2005 |
| WO | 2007/147145 A2 | 12/2007 |
| WO | 2009/086208 A2 | 7/2009 |
| WO | 2011/038291 A1 | 3/2011 |
| WO | 2011/053555 A1 | 5/2011 |
| WO | 2012/120138 A1 | 9/2012 |
| WO | 2012/145431 A3 | 10/2012 |
| WO | 2012/171478 A1 | 12/2012 |
| WO | 2013/158781 | 10/2013 |
| WO | 2015/153996 A1 | 10/2015 |
| WO | 2015/167751 A1 | 11/2015 |
| WO | 2015/167752 A1 | 11/2015 |

OTHER PUBLICATIONS

Edleman et al., Controlled and modulated release of basic fibroblast growth factor. Biomaterials, vol. 12, pp. 619-626 (1991).

Elbert et al., Conjugate addition reactions combined with free-radical cross-linking for the design of materials for tissue engineering. Biomacromolecules, (2): 430-441 (2001).

European Search Opinion for EP Application No. 10819570 dated Mar. 31, 2014.

European Search Opinion for EP Application No. 10827370 dated Apr. 1, 2014.

Graves et al., Endovascular occlusion of the carotid or vertebral artery with temporary proximal flow arrest and mircocoils: clinical results. AJNR Am. J. Neuroradiol., vol. 18, pp. 1201-1206 (1997).

Hoekstra, D., Hyaluronan-modified surfaces for medical devices. Medical Device & Diagnostic Industry, pp. 48-56 (1999).

Hogg et al. Interaction of platelet-derived growth factor with thrombospondin 1. Biochem. J. 326, pp. 709-716 (1997).

Horak et al., Hydrogels in endovascular embolization. II. Clinical use of spherical particles. Biomaterials, 7(6): 467-470 (1986).

Horak et al., New radiopaque polyHEMA-based hydrogel particles. J. Biomed. Matter Res., 34(2): 183-188 (1997).

Huang, et al., "Synthesis and Characterization of Self-Assembling Block Copolymers Containing Adhesive Molecules," Polymer Preprints, vol. 42, No. 2, 2001, pp. 147-148.

International Search Report dated Dec. 17, 2010 for International Patent Application No. PCT/US2010/053972.

(56) References Cited

OTHER PUBLICATIONS

International Search Report dated Feb. 5, 2009 for International Patent Application No. PCT/US2007/071395.
International Search Report dated Aug. 14, 2013 for International PCT Application No. PCT/US2013/037007 filed on Apr. 17, 2013.
International Search Report and Written Opinion dated Jun. 29, 2015 for International Application No. PCT/US2015/024289 filed on Apr. 3, 2015.
International Search Report and Written Opinion dated Jun. 29, 2015 for International Application No. PCT/US2015/024290 filed on Apr. 3, 2015.
International Search Report and Written Opinion dated Jul. 14, 2015 for International Application No. PCT/US2015/024284 filed on Apr. 3, 2015.
Kim, Drug release from pH-sensitive interpenetrating polymer networks hydrogel based on poly (ethylene glycol) Macromer and Poly (acrylic acid) prepared by UV Cured Method, ArchPharmRes, vol. 19(1), 1996, p. 18-22.
Klier, Self Associating Networks of Poly(methacrylic acid g-ethylene glycol) Marcomolecules 1990, vol. 23, 1990, p. 4944-4949.
Larsen et al., Hylan gel composition for percutaneous embolization. Journal of Biomedical Materials Research, vol. 25, Issue 6, pp. 699-710 (1991).
Latchaw et al., Polyvinyl foam embolization of vascular and neoplastic lesions of the head, neck, and spine. Radiology, 131: 669-679 (1979).
Li, Jian et al., Preparation of PEG/Aac copolymerric hydrogel and study of pH-sensitivity. Chemistry World, Issue 1, pp. 20-23 (2005).
Mellott, Michael B. et al., Release of protein from highly cross-linked hydrogels of poly(ethylene glycol) diacrylate fabricated by UV polymerization. Biomaterials, 22(2001) 929-941.
Murayama et al., Cellular responses of bioabsorbable polymeric material and guglielmi detachable coil in experimental aneurysms. Stroke, pp. 1120-1128 (2002).
Persidis, A., Tissue engineering. Nature Biotechnology, 17, pp. 508-510 (1999).
Schmutz et al., Embolization of cerebral arteriovenous malformations with silk: histopathologic changes and hemorrhagic complications. AJNR Am. J. Neuroradiol., vol. 18, pp. 1233-1237 (1997).
Schoenmakers, The effect of the linker on the hydrolysis rate of drug-linked ester bonds, J. Cont. Rel., 95, 2004, pp. 291-300.
Supplementary European Search Report for Ep Application No. 10819570 dated Mar. 31, 2014.
Supplementary European Search Report for EP Application No. 10827370 dated Apr. 1, 2014.
Vinlela et al., Guglielmi detachable coil embolization of acute intracranial aneurysm: perioperative anatomical and clinical outcome in 403 patients. J. Neurosurg., vol. 86, pp. 475-482 (1997).
Woerly et al., Intracerebral implantation of hydrogel-coupled adhesion peptides: tissue reaction. Journal of Neural Transplantation & Plasticity, vol. 5, No. 4, pp. 245-255 (1995).
Written Opinion dated Aug. 14, 2013 for International PCT Application No. PCT/US2013/037007 filed on Apr. 17, 2013.
Zollikofer et al., A combination of stainless steel coil and compressed ivalon: a new technique for embolization of larger arteries and arteriovenous fistulas. Radiology, 138: 229-231 (1981).
Zollikofer et al., Therapeutic blockade of arteries using compressed invalon. Radiology, 136: 635-640 (1980).
U.S. Appl. No. 14/678,514, filed Apr. 3, 2015.
U.S. Appl. No. 14/678,525, filed Apr. 3, 2015.
International PCT Application PCT/US2015/024289 filed on Apr. 3, 2015.
International PCT Application PCT/US2015/024290 filed on Apr. 3, 2015.
International PCT Application PCT/US2015/024284 filed on Apr. 3, 2015.
Son et al., Preparation of properties of PEG-modified PHEMA hydrogel and the morphological effect. Macromolecular Research, vol. 14, No. 3, pp. 394-399 (2006).

* cited by examiner

POLYMERS

CROSS REFERENCE TO RELATED APPLICATIONS

This application claims the benefit of U.S. Provisional Patent Application No. 61/986,018, filed Apr. 29, 2014, the entire disclosure of which is incorporated herein by reference.

FIELD

The present description provides polymer filaments for biomedical treatment, such as the embolization of blood vessels and vascular defects.

SUMMARY

Described herein generally are polymer and/or hydrogel filaments. These polymers and/or hydrogels can be configured for embolization. For example, embolic devices can be formed from the filaments and deployed, repositioned, and detached within the vasculature using practices and microcatheters to occlude blood flow. In some embodiments, the filaments can be used for the embolization of vascularized tumors or arteriovenous malformations. In other embodiments, the filaments can be delivered in such a manner not to substantially occlude flow through a vessel or other lumen.

In one embodiment, the filaments can be sized to deploy, and optionally reposition, through microcatheters with inner diameters ranging from 0.006" to 0.028." In other embodiments, the filaments can be sized to deploy, and optionally reposition, through 4 French (Fr) and larger catheters.

In one embodiment, the filaments can be loaded with visualization agents to impart visibility under fluoroscopy, computed tomography, and/or magnetic resonance imaging. For example, in one embodiment, metallic powders can be added to the filaments to impart fluoroscopic visibility. In another embodiment, the polymer filaments can be loaded with barium sulfate or iodine to impart fluoroscopic visibility and computed tomography (CT) compatibility. In still other embodiments, the filaments can be loaded with gadolinium or superparamagnetic iron oxide particles to impart visibility when imaged by a magnetic resonance scanner. In yet another embodiment, the filaments can be loaded with barium sulfate and superparamagnetic iron oxide particles to impart visibility with fluoroscopy, computed tomography, and/or magnetic resonance imaging.

In one embodiment, the filaments can be releasably attached to a delivery pusher. After repositioning, if desired, and placement in the vasculature through a microcatheter or catheter, a filament can be detached from the delivery pusher. The delivery pusher can then be removed.

In one embodiment, the filaments can be biostable and not susceptible to degradation. Alternatively, in another embodiment, the filaments can be biodegradable. If biodegradable, the filaments may be configured to controllably dissolve.

In one embodiment, fluid uptake by the polymer filament can occur and an increase in filament volume can occur. In another embodiment, a small amount of fluid uptake by the filaments may occur and a small increase in filament volume may occur. In yet another environment, no fluid uptake by the filaments occurs and the filament volume remains unchanged.

DETAILED DESCRIPTION

Figure 1:
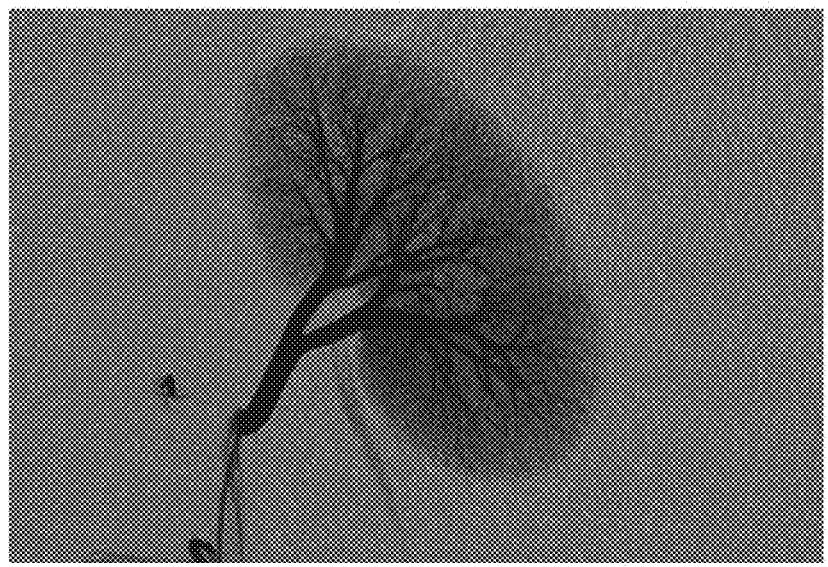
FIG. 1 is a pre-treatment angiography of an implanted pig.

Described herein are polymers such as hydrogels formed as filaments. The polymers can include at least two different macromers. For example, a polymer can include a multifunctional, low molecular weight, ethylenically unsaturated, shapeable macromer, and a difunctional, ethylenically unsaturated macromer. The polymers can optionally include one or more visualization agents. The filaments can include polymers with different polymeric physical properties such as, but not limited to, varying tensile strength and/or elasticity.

The polymers described herein can be provided as filaments or other elongated structures with round, square, rectangular, triangular, pentagonal, hexagonal, heptagonal, octagonal, ellipsoidal, rhomboidal, torx, or star cross-sectional shapes. A filament can be described as having a three dimensional shape such as, but not limited to a thread, string, hair, cylinder, fiber, or the like. The filament can be elongated meaning that its length exceeds its width or diameter by at least 5, 10, 15, 20, 50, 100, 500, 1,000 or more times.

The polymers described can be formed from a prepolymer solution. A particular combination of macromers can be dispersed in a solvent to form the prepolymer solution. The prepolymer solution can also include initiators and/or visualization agents.

As discussed, one of the at least two different macromers can be a multifunctional, low molecular weight, ethylenically unsaturated, shapeable macromer. In some embodiments, this is referred to as a first macromer. This first macromer can impart mechanical properties to the filaments as well as provide the bulk structural framework for the filament. In one embodiment, polymers with solubility in solvents and functional groups amenable to modifications can be preferred. A first macromer can be a polyether. Polyethers have solubility in a variety of solvents, are available in a variety of forms, and are available with hydroxyl groups. First macromers provided as polyethers can be poly(ethylene glycol), poly(propylene glycol), poly(tetramethylene oxide), ethoxylated pentaerthritol, and ethoxylated pentaerythritol tetra-acrylamide. In one embodiment, the first macromer is ethoxylated pentaerthritol and it can have a low molecular weight and four hydroxyl groups.

In other embodiments, the first macromer can be a non-polyether polymer with functional groups available for modification. Such non-polyether macromers can include poly(vinyl alcohol).

The first macromer can have a concentration from about 5% to about 50% w/w, about 15% to about 25% w/w, about 10% to about 30% w/w, about 20% to about 25% w/w, or about 15% to about 20% w/w of the prepolymer solution. In one embodiment, the first macromer has a concentration of about 20% w/w of the prepolymer solution.

The molecular weight of the first macromer can alter the mechanical properties of the resulting polymer or hydrogel filament. In some embodiments, the alteration of the mechanical properties can be substantial. Smaller molecular weights result in polymers with sufficient column strength to be pushed through microcatheters and catheters when formed as a filament or other elongated structures. Larger molecular weights can result in polymer filaments that can be pushed through microcatheters and catheters with more difficulty. As such, the first macromer can have a molecular weight of about 50 g/mole, about 100 g/mole, about 200 g/mole, about 300 g/mole, about 400 g/mole, about 500 g/mole, about 700 g/mole, about 1,000 g/mole, about 1,500 g/mole, about 2,000 g/mole, about 2,500 g/mole, about 3,000 g/mole, about 3,500 g/mole, about 4,000 g/mole, about 4,500 g/mole, about 5,000 g/mole, at least about 50 g/mole, at least about 100 g/mole, between about 50 g/mole and about 5,000 g/mole, between about 100 g/mole and about 5,000 g/mole, between about 1,000 g/mole and about 5,000 g/mole, between about 100 g/mole and about 1,000 g/mole, between about 700 g/mole and about 1,000 g/mole, or between about 500 g/mole and about 1,000 g/mole. In one embodiment, the molecular weight is between about 700 g/mole to about 1,000 g/mole.

The functional groups of the first macromer can be derivatized to impart ethylenically unsaturated moieties to allow free radical polymerization. Preferred functionalities for free radical polymerization can include acrylate, acrylamides, methacrylamides, methacrylates, vinyl groups, and derivatives thereof. In some embodiments, functionalities for free radical polymerization can include alkylacrylate and alkylacrylamide, wherein alkyl can be a methyl, ethyl, propyl, butyl, pentyl, hexyl, heptyl, or octyl linear or branched alkyl group. Alternatively, other reactive chemistries can be employed to polymerize the polymer, i.e. nucleophile/N-hydroxysuccinimide esters, vinyl sulfone/acrylate or maleimide/acrylate. In one embodiment, a first macromer functional group can be an acrylate.

The second of the at least two different macromers, the second macromer, can be a difunctional, ethylenically unsaturated macromer. In some embodiments, the second macromer can be referred to as a flexomer. The flexomer can add flexibility and/or elasticity to the resulting polymer or hydrogel filament. This flexibility can enable functionality of the hydrogel filaments for use in devices such as detachable embolic devices. In general any polymer that can provide the flexibility can function as a flexomer. However, in some embodiments, polymers with solubility in solvents and functional groups amenable to modifications may be preferred.

Flexomers can be polyethers because of their solubility in a variety of solvents, their availability in a variety of forms, and their available hydroxyl groups. A flexomer can be selected from poly(ethylene glycol), poly(propylene glycol), poly(tetramethylene oxide), linear polyethylene glycol and combinations thereof. Non-polyether polymers with functional groups available for modification, such as poly(vinyl alcohol), can also be utilized as a flexomer.

Flexomer concentrations can be about 0.01% w/w, about 0.05% w/w, about 0.1% w/w, about 0.2% w/w, about 0.3% w/w, about 0.4% w/w, about 0.5% w/w, about 0.6% w/w, about 0.7% w/w, about 0.8% w/w, about 0.9% w/w, about 1% w/w, about 1.5% w/w, about 2% w/w, about 2.5% w/w, about 3% w/w, about 3.5% w/w, about 4% w/w, about 4.5% w/w, about 5% w/w, between about 0.1% w/w and about 1% w/w, between about 0.01% w/w and about 2% w/w, between about 0.5% w/w and about 3% w/w, between about 1% w/w and about 5% w/w, at least about 0.01% w/w, at most about 0.01% w/w, or at most about 2% w/w of the prepolymer solution. In one embodiment, the flexomer concentration can be about 0.2% w/w of the prepolymer solution. In another embodiment, the flexomer concentration can be about 2.5% w/w of the prepolymer solution.

In some embodiments, the first macromer has a concentration about 5 times, about 6 times, about 8 times, about 10 times, about 15 times, about 20 times, about 25 times, about 50 times, greater than about 5 times, greater than about 10 times, or greater than about 15 times the flexomer concentration in the prepolymer solution.

The molecular weight of the flexomer can alter the mechanical properties of the resulting filament. Smaller molecular weights can result in filaments with sufficient column strength but insufficient flexibility to be pushed through microcatheters and catheters. Larger molecular weights can result in filaments with sufficient flexibility but insufficient column strength that can be pushed through microcatheters and catheters.

As such, the second macromer or flexomer can have a molecular weight of about 500 g/mole, about 1,000 g/mole, about 2,000 g/mole, about 3,000 g/mole, about 4,000 g/mole, about 5,000 g/mole, about 6,000 g/mole, about 7,000 g/mole, about 8,000 g/mole, about 9,000 g/mole, about 10,000 g/mole, about 11,000 g/mole, about 12,000 g/mole, about 13,000 g/mole, about 14,000 g/mole, about 15,000 g/mole, about 16,000 g/mole, about 17,000 g/mole, about 18,000 g/mole, about 19,000 g/mole, about 20,000 g/mole, at least about 500 g/mole, at least about 1,000 g/mole, between about 500 g/mole and about 20,000 g/mole, between about 1,000 g/mole and about 10,000 g/mole, between about 8,000 g/mole and about 12,000 g/mole, between about 4,000 g/mole and about 20,000 g/mole, between about 7,000 g/mole and about 10,000 g/mole, or between about 5,000 g/mole and about 15,000 g/mole. In one embodiment, the molecular weight of the flexomer can be between about 8,000 g/mole to about 12,000 g/mole.

In some embodiments, the flexomer has a molecular weight about 5 times, about 6 times, about 8 times, about 10 times, about 15 times, about 20 times, about 25 times, about 50 times, greater than about 5 times, greater than about 10 times, or greater than about 15 times the first macromer concentration in the prepolymer solution.

In some embodiments, an initiator can be used to start polymerization of the polymerizable components of the prepolymer solution. The prepolymer solution can be polymerized by reduction-oxidation, radiation, heat, or any other known method. Radiation cross-linking of the prepolymer solution can be achieved with ultraviolet light or visible light with suitable initiators or ionizing radiation (e.g. electron beam or gamma ray) without initiators. Cross-linking can be achieved by application of heat, either by conventionally heating the solution using a heat source such as a heating well, or by application of infrared light to the prepolymer solution.

Free radical polymerization of the prepolymer solution in some embodiments is preferred and may require an initiator to start the reaction. In a preferred embodiment, the cross-linking method utilizes azobisisobutyronitrile (AIBN) or another water soluble AIBN derivative (2,2'azobis(2-methylpropionamidine)dihydrochloride). Other useful initiators can include N,N,N',N'-tetramethylethylenediamine, ammonium persulfate, benzoyl peroxides, and combinations thereof, including azobisisobutyronitriles. Initiator concentrations can be about 1% w/w, about 2% w/w, about 3% w/w, about 4% w/w, about 5% w/w, between about 0.5% w/w and about 5% w/w, between about 1% w/w and about 3% w/w, or between about 2% w/w and about 3% w/w. In one embodiment, azobisisobutyronitrile is used as an initiator.

Biostability or biodegradation can be imparted to the resulting hydrogel by altering the synthetic route of derivatizing the functional groups of the first macromer. If biostability is desired, linkage stability in the physiological environment can be utilized. In one embodiment, a biostable linkage can be an amide. A hydroxyl group of the macromer can be converted to an amino group followed by reaction with acryloyl chloride to form an acrylamide group. In one embodiment, a first macromer can be ethoxylated pentaerythritol tetra-acrylamide with a molecular weight of about 1,000 g/mole.

If biodegradation is desired, linkages susceptible to breakage in a physiological environment can be utilized. Preferred biodegradable linkages include esters, polyesters, and amino acid sequences degradable by enzymes.

Polymer filaments can be made to be visible using medically relevant imaging techniques such as fluoroscopy, computed tomography, or magnetic resonant imaging to permit intravascular delivery and follow-up. Visualization of the polymer filaments under fluoroscopy can be imparted by incorporating solid particles of radiopaque materials such as barium, bismuth, tantalum, platinum, gold, and other dense metals into the polymer or by polymerizing iodine-containing molecules into the polymer filament. Visualization agents for fluoroscopy can include barium sulfate and iodine-containing molecules.

In other embodiments, polymer visualization under computed tomography imaging can be imparted by incorporation of solid particles of barium or bismuth or by the incorporation of iodine-containing molecules polymerized into the polymer structure of the filament.

Metals visible under fluoroscopy can sometimes result in beam hardening artifacts that may preclude the usefulness of computed tomography imaging for medical purposes.

If used as a visualization agent to render the polymer visible using fluoroscopic and computed tomography imaging, barium sulfate can be present at a concentration of about 20% w/w, about 30% w/w, about 40% w/w, about 50% w/w, about 60% w/w, about 70% w/w, at least about 20% w/w, between about 30% w/w and about 60% w/w, between about 20% w/w and about 70% w/w, or between about 40% w/w and about 50% w/w of the prepolymer solution. In one embodiment, barium sulfate is present at a concentration between about 40% w/w and about 60% w/w of the prepolymer solution.

In some embodiments, the polymer can be visualized using fluoroscopic and computed tomography imaging when it includes about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, at least about 100 mg, at least about 125 mg, at least about 150 mg, between about 100 mg and about 500 mg, between about 125 mg and about 300 mg, or between about 100 mg and about 300 mg of iodine per gram of polymer.

In some embodiments, iodine associated with a monomer included in the hydrogel. For example, a monomer can include one, two, three, four, five, or more iodine atoms per monomer. In some embodiments, additional iodine containing monomers can be included in the solutions used to form the herein described hydrogels. Further, in some embodiments, iodine can be associated with or otherwise attached to any of the macromers or flexomers described herein and polymerized into the hydrogels.

Visualization of the filaments under magnetic resonance imaging can be imparted by incorporation of solid particles of superparamagnetic iron oxide or gadolinium molecules polymerized into the polymer structure. In one embodiment, a preferred visualization agent for magnetic resonance is superparamagnetic iron oxide. The particle size of the solid particles can be about 5 µm, about 10 µm, about 15 µm, about 20 µm, about 25 µm, between about 10 µm and about 25 µm, or between about 5 µm and about 15 µm. Concentrations of superparamagnetic iron oxide particles to render the hydrogel visible using magnetic resonance imaging range from 0.1% to 1% w/w of the prepolymer solution.

Methods of forming the polymer filaments are also described. Methods of forming polymer filaments or other elongated structures can comprise reacting a prepolymer solution including at least two different macromers and at least one visualization agent.

In another embodiment, methods of forming polymer filaments or other elongated structures can comprise reacting a prepolymer solution including at least one first macromer, at least one different second macromer, and at least one visualization agent.

In another embodiment, methods of forming polymer filaments or other elongated structures can comprise reacting a prepolymer solution including at least one first macromer, at least one flexomer, and at least one visualization agent.

The resulting polymer filament can be prepared for implantation. After formation, the polymer filament can be loaded into a support member. The support member can be formed of a metal. In other embodiments, the support member is not formed of a metal, but rather formed of a material such as a plastic or other polymer. In other embodiments, the polymer filaments do not require any support members to be delivered.

For example, to prepare a polymer such as in the shape or form of a filament or other elongated structure, a tubular extrusion is filled with prepolymer solution. The extrusion is the mold for the filament. In some embodiments, if one of the components is solid, a solvent will be utilized in the preparation of the filaments. If liquid components are utilized, a solvent may not be required, but may be desired.

Any aqueous or organic solvent may be utilized that fully dissolves the desired macromers, soluble visualization agents, and optional polymerization initiators. The solvent can completely dissolve or suspend all macromers, initiators, and visualization agents. If a liquid macromer(s) is used, a solvent may not be necessary. The solvent, if necessary, is selected based on the solubility of the components of the polymerization solution. Preferred solvents can be dimethylformamide, isopropanol, ethanol, water, dichloromethane, and acetone. However, a number of solvents can be utilized.

Concentrations of the solvent can be between about 40% w/w to about 80% w/w, between about 50% w/w to about 60% w/w, between about 40% w/w to about 70% w/w, between about 50% w/w to about 80% w/w, or between about 40% w/w to about 60% w/w of the prepolymer solution. In one embodiment, the solvent is present at between about 50% w/w and about 60% w/w.

In some embodiments, the prepolymer solution is prepared by placing the macromers, or macromer and flexomer, optional visualization agent, and initiator in the solvent. After dissolution of these components, an insoluble visualization agent, such as barium sulfate or superparamagnetic iron oxide particles, can be suspended in the prepolymer solution. In other embodiments, this insoluble visualization agent is not used. Mixing of the prepolymer solution containing an insoluble visualization agent with a homogenizer can aid the suspension of the insoluble visualization agent.

The prepolymer solution can then be injected into tubing with an inner diameter ranging from 0.015 cm to 0.19 cm and incubated for several hours at an elevated temperature or in boiling water, i.e. 100° C., and subsequently overnight at 80° C. to complete polymerization. Immersion in boiling water allows for rapid heat transfer from the water to the prepolymer solution contained in the tubing.

The selection of the tubing imparts microcatheter or catheter compatibility. For delivery through microcatheters, tubing diameters from about 0.006 in to about 0.028 in, or 0.006 in to about 0.025 in can be used. In one embodiment, the tubing is made from HYTREL® (DuPont, Wilmington, Del.). The HYTREL® tubing can be dissolved in solvents, facilitating removal of a polymer filament from the tubing.

In another embodiment, the tubing may be peelable PTFE tubing. PTFE, as well as other fluoropolymers, can be ram-extruded to form tubing. In some embodiments, because the molecules of the tubing do not recrystallize as with thermoplastics, they may be more inclined to tear in the direction in which they were extruded.

If the tubing is wrapped around a mandrel prior to polymerization of the prepolymer solution, the resulting hydrogel filament maintains the shape of the wrapped tubing. Using this wrapping technique, helical, tornado, and complex shapes can be imparted to the finalized filaments. When the tubing is wrapped around a mandrel, the use of oval tubing may be preferred. After wrapping around the mandrel, the oval shape of the tubing is rounded and the resulting hydrogel filament has a round shape in the coiled configuration.

If HYTREL® tubing is utilized, the hydrogel filament can be recovered by incubating the tubing in a solution of 20% w/w phenol in chloroform followed by washing in chloroform and ethanol. After the filament is washed, it is dried.

If peelable PTFE tubing is utilized, the filament can be recovered by nicking the tube with a razor blade and peeling along its longitudinal axis. Once removed, the filament is washed, for example, in ethanol. After the hydrogel has been washed, it is dried and a dried hydrogel filament is produced.

Filaments or other elongated structures formed using the present methods can vary in length depending on the method parameters used. However, generally, filament lengths can range from about 0.5 cm to about 100 cm, about 1 cm to about 50 cm, about 10 cm to about 100 cm, or about 0.5 cm to about 25 cm. Likewise diameters can vary. For example, diameters can be about 0.010 cm to about 0.50 cm, about 0.015 cm to about 0.19 cm, or about 0.010 cm to about 0.20 cm.

After recovery and washing of the filament, it is fabricated into a device suitable for use by a physician, surgeon, or other practitioner. If a repositionable device is desired, a length of filament is inserted into a tube slightly larger than the filament's diameter. This straightens the secondary shape of the filament and permits the gluing of a poly(ether-etherketone) coupler to one end of the filament. Subsequently the coupler is attached to a pusher, packaged, and sterilized.

Upon receipt, the physician introduces the filament into a microcatheter or catheter and then pushes it through the microcatheter or catheter to an embolization or other medically relevant site. The filament can be advanced and withdrawn until the physician is satisfied with its position. Then the filament can be detached from the pusher.

If a pushable device is desired, a dried hydrogel filament is loaded into an introducer, packaged in a suitable pouch, and sterilized. Upon receipt, the physician transfers the hydrogel from the introducer to a microcatheter or catheter using a guide wire, a stylet, or a fluid injection. The dried filament is then pushed through the microcatheter or catheter and into an embolization site or other medically relevant site using a guide wire or a fluid injection.

Example 1

Preparation of Ethoxylated Pentaerythritol Tetra-Acrylamide

First, 500 g of pentaerythritol ethoxylate (PE) 797 was dried by azeotropic distillation with 3,750 mL of toluene. Then, 248.9 g of triethylamine were added with 281.8 g of mesyl chloride and stirred for 12 hours. The solution was then filtered to remove salt and the solvent evaporated. The resulting product was added to 1,250 mL of acetonitrile and 1,250 mL of 25% ammonia hydroxide and stirred for 3 days. All but 1,000 mL of water was evaporated and the pH was adjusted to 13 with NaOH. The solution was extracted with dichloromethane, dried over magnesium sulfate, filtered, and the solvent evaporated.

To 250 g of the resulting pentaerythritol ethoxylateamine, 2,500 mL of dichloromethane was added along with 325 g of sodium carbonate. The solution was cooled in an ice bath and 88.5 mL of acryloyl chloride and stirred for 18 hours. The solution was filtered to remove salt and the solvent evaporated. The resulting ethoxylated pentaerythritol tetraacrylamide was suspended in water, the pH was adjusted to 13 with NaOH, extracted with dichloromethane, dried over magnesium sulfate, filtered, the solvent removed by rotary evaporation, and purified over a silica column.

Example 2

Preparation of Polyethylene Glycol Diacrylamide

Three hundred thirty grams of polyethylene glycol (PEG) 8,000 was dried by azeotropic distillation with 1,900 mL of toluene. Then, 90 mL of dichloromethane, 12.5 mL of triethylamine was added with 9.3 mL of mesyl chloride and stirred for 4 hr. The solution was filtered, the product precipitated in diethyl ether, and then collected by filtration. The resulting product was vacuum dried and then added to 2,000 mL of 25% ammonia hydroxide and stirred closed for 4 days, then open for 3 days. All but 200 mL of water was evaporated and the pH was adjusted to 13 with NaOH. The solution was extracted with dichloromethane, dried over magnesium sulfate, filtered and all but 200 mL of solvent evaporated. To the resulting PEG diamine in dichloromethane was added 1,200 mL of toluene, 12.5 mL of triethylamine and 9.0 mL of acryloyl chloride and the reaction was stirred for 4 hr. The resulting solution was filtered, precipitated in ether, and the solvent removed yielding PEG 8,000 diacrylamide.

Example 3

Preparation of Hydrogel Filament-Fluoroscopy

To prepare a hydrogel filament visible under fluoroscopy, 4.0 g pentaerythritol tetra-acrylamide, 0.35 g of polyethylene glycol 8,000 diacrylamide and 0.05 g 2,2'-azobisisobutyronitrile were dissolved in 2.5 g of dimethylformamide. The solution was filtered through a 0.2 micron filter. To 6.65 g of solution, 8.0 g of barium sulfate was added. The solution was sparged with argon for 10 minutes before injection into oval HYTREL tubing wrapped around a mandrel. The tubes were heat sealed at both ends and placed in a 100° C. water bath for 1 hour, then overnight in an 80° C. oven to polymerize the solution.

The hydrogel was removed by dissolving the tubing in a solution of 20% phenol in chloroform. After the tubing was removed, the phenol solution was exchanged with chloroform and washed for 1 hour. After 1 hr, the chloroform was exchanged and the hydrogel washed for another 1 hr. The chloroform was removed and the hydrogel dried in a vacuum oven for 2 hr at 50° C. To remove any unreacted monomers, the hydrogel was placed in ethanol for 12 hr. After 12 hr, the ethanol was exchanged and washed for 2 hr. After 2 hr, the ethanol was exchanged and the hydrogel washed for another 2 hr. The ethanol was removed and hydrogel dried in a vacuum oven for 12 hr.

Example 4

Preparation of Hydrogel Filament

To prepare a hydrogel filament visible under fluoroscopy, 4.0 g pentaerythritol tetra-acrylamide, 0.10 g of polyethylene glycol 8,000 diacrylamide and 0.05 g 2,2'-azobisisobutyronitrile were dissolved in 2.5 g of dimethylformamide. The solution was filtered through a 0.2 micron filter. To 6.65 g of solution, 8.0 g of barium sulfate was added. The solution was sparged with argon for 10 minutes before injection into oval HYTREL tubing wrapped around a mandrel. The tubes were heat sealed at both ends and placed in a 100° C. water bath for 1 hour, then overnight in an 80° C. oven to polymerize the solution.

The hydrogel was removed by dissolving the tubing in a solution of 20% phenol in chloroform. After the tubing was removed, the phenol solution was exchanged with chloroform and washed for 1 hour. After 1 hr, the chloroform was exchanged and the hydrogel washed for another 1 hr. The chloroform was removed and the hydrogel dried in a vacuum oven for 2 hr at 50° C. To remove any unreacted monomers, the hydrogel was placed in ethanol for 12 hr. After 12 hr, the ethanol was exchanged and washed for 2 hr. After 2 hr, the ethanol was exchanged and the hydrogel washed for another 2 hr. The ethanol was removed and hydrogel dried in a vacuum oven for 12 hr.

Example 5

Preparation of Hydrogel Filament Device

The radiopaque hydrogel filament of Example 3 can be attached to a V-TRAK® (MicroVention Terumo, Inc., Tustin, Calif.). To attach the hydrogel to a V-TRAK pusher, a section of 0.0022 inch polyolefin thread was threaded through a coupler. The coupler consisted of a PEEK cylinder hollowed out on one end to accept the hydrogel filament and a through hole. The polyolefin thread was tied into a knot such that it could not be pulled back through. The hydrogel was glued into the coupler on top of the knot using adhesive. The other end of the polyolefin thread was threaded into a V-TRAK pusher and tied.

Example 6

In Vivo Evaluation of Hydrogel Filament Device

Figure 2:
FIG. 2 is a post treatment angiography of the implanted pig.
Figure 3:
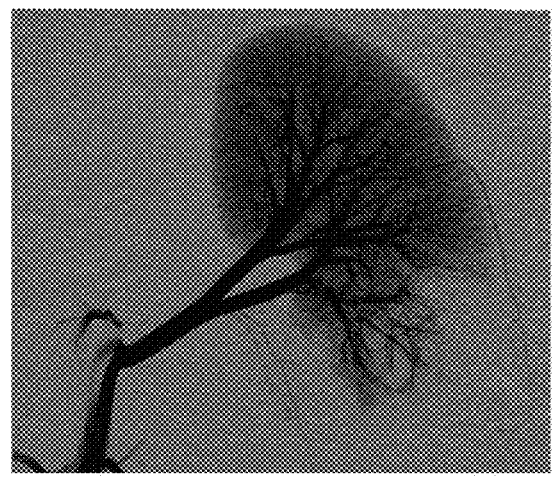
FIG. 3 is a 7-day post treatment angiography of the implanted pig.
Figure 4:
FIG. 4 illustrates a CT angiography post embolization of the renal artery of one of the animals from Example 5.

The renal, gluteal and profunda arteries of three pigs were embolized with radiopaque polymer filaments as described in Example 3 and the V-TRAK pusher of Example 5. Under fluoroscopic guidance, a microcatheter (PROGREAT® 2.4 Fr, Terumo Medical Corporation, Somerset, N.J.) was placed inside the renal, gluteal and profunda artery of each animal. Several hydrogel filaments were deployed inside the artery lumen to achieve occlusion. All six arteries were embolized completely post-treatment. At one week post embolization, stable occlusion was demonstrated by angiography as illustrated in FIGS. 1-3. FIG. 3 shows that occlusion has been established and is present 7 days after implantation. Angiography also demonstrated that one month post embolization, stable occlusion existed.

Example 7

CT Evaluation of Hydrogel Filament Device

One of the three animals embolized with radiopaque polymer filaments underwent CT angiography post embolization of the renal artery (See FIG. 2). CT was performed using a Philips Allura X per FD20 Imaging System. When imaged, the beam hardening artifacts of the hydrogel filaments were greatly reduced compared to platinum coils. The vessel lumen and the stability of the polymer filaments inside the lumen were able to be assessed using CTA. These results illustrate that CTA imaging is suitable for determining the embolic stability and whether retreatment is necessary for vessels embolized with radiopaque hydrogel filaments.

Example 8

In Vitro Evaluation of Mechanical Properties

The ultimate tensile strength and percent elongation of hydrogel filaments prepared with and without a flexomer were obtained using an Instron 5543 tensile tester. The ultimate tensile strength and percent elongation at which the filament broke was measured one hour after hydration with 0.9% saline (full hydration). The average of three to five replicates each are summarized in Table 1 along with previously disclosed Azur Pure formulations.

TABLE 1

| Sample | Flexomer | Tensile Strength (lbf) Hydrated | % Elongation Hydrated |
|---|---|---|---|
| 1 | PEG 8,000 | 0.214 ± 0.040 | 20.7 ± 4.5 |
| 2 | None | 0.158 ± 0.023 | 12.7 ± 2.8 |
| 3 | None | 0.111 ± 0.018 | 21.5 ± 9.4 |

The results illustrate that the addition of the flexomer to the filament increases its elongation and ultimate tensile strength over filaments without flexomer. In other words, the addition of a flexomer can provide a filament with both an increased tensile strength and increased flexibility. Previous filaments had either increased tensile strength, e.g., Sample 2, or increased flexibility, e.g., Sample 3, but not both.

The expansion characteristics of the polymer filaments were determined using a video inspection station. First, the dry diameter of the polymer filament section was measured. Then, the polymer was exposed to phosphate buffered saline for one hour and the diameter re-measured. The average of three to five replicates each are summarized in Table 2 along with a previously disclosed Azur Pure formulation.

TABLE 2

| Sample | Flexomer | Diameter (in) Dry | Diameter (in) Hydrated | Percent Expansion |
|---|---|---|---|---|
| 1 | PEG 8,000 | 0.016 ± 0.0001 | 0.018 ± 0.0002 | 11.0 |
| 2 | None | 0.017 ± 0.0004 | 0.018 ± 0.0001 | 8.4 |
| 3 | None | 0.016 ± 0.0002 | 0.018 ± 0.0001 | 12.4 |

The results illustrate the addition of the flexomer does not appreciably alter the expansion of the filament despite the increase in tensile strength and flexibility described above.

Example 9

In Vitro Evaluation of Deployment and Repositioning

Azur Pure hydrogel filaments and hydrogel filaments with flexomer were attached to V-TRAK pushers and deployed in a silicone vascular model to test pushability, retractability and repositioning time using standard microcatheter techniques. The pushability and retractability were scored from poor to excellent. The data of three to five replicates each are summarized in Table 3.

TABLE 3

| Sample | Flexomer | Size | Pushability | Retractability | Response Time |
|---|---|---|---|---|---|
| Azur Pure | None | 4 mm × 15 cm | Poor | Poor | <1 min |
|  |  | 5 mm × 15 cm | Good | Poor | <1 min |
|  |  | 10 mm × 15 cm | Good | Poor | <2 min |
| M-288 | PEG 8,000 | 4 mm × 20 cm | Excellent | Excellent | >5 min |
|  |  | 5 mm × 15 cm | Excellent | Excellent | >5 min |
|  |  | 10 mm × 20 cm | Excellent | Excellent | >5 min |

The Table 3 results illustrate that the addition of a flexomer can increase the pushability, retractability, and repositioning time of the filaments, even at longer lengths.

Unless otherwise indicated, any numbers expressing quantities of ingredients, properties such as molecular weight, reaction conditions, and so forth used in the specification and claims are to be understood as being modified in all instances by the term "about." Accordingly, unless indicated to the contrary, any numerical parameters set forth in the following specification and attached claims are approximations that may vary depending upon the desired properties sought to be obtained by the present invention. At the very least, and not as an attempt to limit the application of the doctrine of equivalents to the scope of the claims, any numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

The use of the term "or" in the claims is used to mean "and/or" unless explicitly indicated to refer to alternatives only or the alternatives are mutually exclusive, although the disclosure supports a definition that refers to only alternatives and "and/or."

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects those of ordinary skill in the art to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above cited references and printed publications are herein individually incorporated by reference in their entirety.

Further, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A polymer filament comprising:
a pentaerythritol and polyethylene glycol copolymer; and
between about 20% w/w and about 70% w/w barium sulfate;
wherein the co-polymer is a reaction product of a prepolymer solution including at least one pentaerythritol macromer and at least one polyethylene glycol flexomer;
wherein the at least one pentaerythritol macromer has a molecular weight between about 700 g/mole to about 1,000 g/mole; and
wherein the at least one polyethylene glycol flexomer has a molecular weight between about 8,000 g/mole to about 12,000 g/mole.

2. The polymer filament of claim 1, wherein the at least one pentaerythritol macromer is a multifunctional, ethynically unsaturated, shapeable macromer.

3. The polymer filament of claim 1, wherein the at least one pentaerythritol macromer is ethoxylated pentaerythritol, ethoxylated pentaerythritol tetra-acrylamide, or combinations thereof.

4. The polymer filament of claim 1, wherein the at least one pentaerythritol macromer is ethoxylated pentaerythritol.

5. The polymer filament of claim 1, wherein the at least one pentaerythritol macromer has a concentration from about 5% to about 50% w/w.

6. The polymer filament of claim 1, wherein the at least one polyethylene glycol flexomer is a difunctional, ethylenically unsaturated polyethylene glycol flexomer.

7. The polymer filament of claim 1, wherein the at least one polyethylene glycol flexomer has a concentration of between about 0.1% w/w and about 1% w/w of the prepolymer solution.

8. The polymer filament of claim 1, wherein the polymer filament does not include metallic support members.

9. The polymer filament of claim 1, wherein the polymer filament is capable of delivery through a catheter.

10. The polymer filament of claim 1, wherein the co-polymer is a co-polymer of a pentaerythritol ethoxylate and a polyethylene glycol.

11. The polymer filament of claim 1, wherein the co-polymer is a co-polymer of a pentaerythritol ethoxylate and a polyethylene glycol diacrylamide.

* * * * *